US012716974B2

(12) United States Patent
Zhu et al.

(10) Patent No.: US 12,716,974 B2
(45) Date of Patent: Aug. 25, 2026

(54) METHOD, SYSTEM AND/OR COMPUTER READABLE MEDIUM FOR IMPROVED MAGNETIC RESONANCE (MR) IMAGING-BASED TRACTOGRAPHY

(71) Applicant: GE Precision Healthcare LLC, Waukesha, WI (US)

(72) Inventors: Ante Zhu, Schenectady, NY (US); Jerome Joseph Maller, Victoria (AU)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 169 days.

(21) Appl. No.: 18/807,168

(22) Filed: Aug. 16, 2024

(65) Prior Publication Data

US 2026/0050054 A1 Feb. 19, 2026

(51) Int. Cl.

| | |
|---|---|
| ***G01R 33/561*** | (2006.01) |
| ***A61B 5/055*** | (2006.01) |
| ***G01R 33/56*** | (2006.01) |
| ***G01R 33/563*** | (2006.01) |

(52) U.S. Cl.

CPC ..... *G01R 33/5616* (2013.01); *G01R 33/5608* (2013.01); *G01R 33/56341* (2013.01); *A61B 5/055* (2013.01)

(58) Field of Classification Search

CPC ............ G01R 33/5608; G01R 33/5616; G01R 33/56341; A61B 5/055

See application file for complete search history.

(56) References Cited

U.S. PATENT DOCUMENTS

| | | | | |
|---|---|---|---|---|
| 9,404,986 | B2 | 8/2016 | White et al. | |
| 10,712,419 | B2 * | 7/2020 | Xu | G01R 33/56341 |
| 12,507,959 | B2 * | 12/2025 | Mostapha | A61B 5/7267 |
| 2010/0298692 | A1 * | 11/2010 | Schmainda | G01R 33/56341 600/410 |

OTHER PUBLICATIONS

Van, et al., In Vivo Investigation of Restricted Diffusion in The Human Brain with Optimized Oscillating Diffusion Gradient Encoding, Magnetic Resonance in Medicine, 2014, pp. 83-94, vol. 71.

(Continued)

*Primary Examiner* — Gregory H Curran

(74) *Attorney, Agent, or Firm* — Daugherty & Del Zoppo, Co. LPA

(57) ABSTRACT

A magnetic resonance (MR) imaging system includes a main magnet configured to generate a magnetic field, gradients coils configured to generate time varying gradient magnetic fields, a radiofrequency (RF) transmit coil configured to generate RF signals, a controller configured to control the gradient and RF transmit coil based on a first sequence that includes a pulse gradient spin echo (PGSE) acquisition and an oscillating gradient spin echo (OGSE) acquisition, an RF receive coil configured to receive first MR signals generated in response to the PGSE and OGSE acquisitions, an image reconstructor configured to process the first MR signals and generate a first apparent diffusion coefficient (ADC) map for the PGSE acquisition and a second ADC map for the OGSE acquisition, and a processor configured to generate a seed point map based on the first and second ADC maps, wherein the seed point map visually distinguishes tumor and vasogenic edema.

20 Claims, 7 Drawing Sheets

(56) References Cited

OTHER PUBLICATIONS

Kamimura, et al., Differentiating Brain Metastasis from Glioblastoma by Time-Dependent Diffusion MRI, Cancer Imaging, 2023, 13 sheets, vol. 23, No. 75.
Baron et al., Oscillating Gradient Spin-Echo (OGSE) Diffusion Tensor Imaging of the Human Brain, Magnetic Resonance in Medicine, 2014, pp. 726-736, vol. 72.
McDonald et al., Recovery of white matter tracts in regions of peritumoral FLAIR hyperintensity with use of restriction spectrum imaging, American Journal of Neuroradiology, Jun. 2013, p. 1157-63, vol. 34, www.ajnr.org.
Zhu, et al., Revealing tumor microstructure with oscillating diffusion encoding MRI in pre-surgical and post-treatment glioma patients, Magnetic Resonance in Medicine, published Jun. 19, 2023, p. 1789-1801, vol. 90; wileyonlinelibrary.com/journal/mrm.

* cited by examiner

800

804

802

METHOD, SYSTEM AND/OR COMPUTER READABLE MEDIUM FOR IMPROVED MAGNETIC RESONANCE (MR) IMAGING-BASED TRACTOGRAPHY

FIELD

The following generally relates to magnetic resonance (MR) imaging, and more particularly to an improved approach for MR imaging-based tractography.

BACKGROUND

Magnetic resonance (MR) imaging is a radiology technology that employs magnetic fields and gradients and radio waves to generate images of the interior of a subject or object. In general, the subject or object is positioned in an examination region within a magnetic field $B_O$ that is generated by a main magnet and that extends in a longitudinal or z-direction, where magnetic moments of nuclei, such as protons, align with the magnetic field and precess about the magnetic field in a random order at the nuclei's Larmor frequency. For image acquisition, an excitation radiofrequency (RF) field $B_1$, which is in a transverse or x-y plane and near the Larmor frequency, is generated by a coil and "flips" the net magnetic moment of the nuclei from the z-direction to the x-y plane. An MR signal is emitted by the nuclei as the magnetic moment returns to the z-direction. Magnetic field gradients (Gx, Gy, and Gz) are employed to encode the MR signals and scan through a k-space, and the MR signals are reconstructed to generate images. MRI applications include diffusion, perfusion, structural, functional, angiography, etc.

An example of a diffusion-based application includes tractography. Tractography, in general, is a technique for visualizing white matter nerve fibers in the brain connecting gray matter based on the diffusion of water molecules. A standard diffusion MR approach for tractography includes acquiring MR data using a pulsed gradient spin echo (PGSE) based diffusion tensor imaging (DTI) sequence and generating a fractional anisotropy (FA) map therefrom, where, in healthy normal tissue, a higher FA value indicates a likely presence of nerve fibers, and a lower FA value indicates a likely absence of nerve fibers. The white matter nerve fiber seed points are then identified in the MR images by a user based on the FA values, knowledge of brain anatomy, etc. A software algorithm then grows nerve fiber tracks from the seed points by evaluating a direction of the fiber at a current location, stepping along this direction by a step size, and then repeating until termination criteria (e.g., the FA value satisfies a stopping threshold) is reached to produce a tractogram that shows directionality and connection of nerve fibers in the brain.

For surgical procedures such as resection of a tumor (solid, infiltrative, etc.) in the brain, the surgeon needs to know if a region can be safely resected without damaging any normal healthy nerve fibers, which could lead to loss of a bodily function. With tumors, the white matter nerve fibers around the tumor may be stretched and the fiber bundles may be disorganized. As such, the FA values in the tumor region and its surrounding are reduced. The underlying histopathology of vasogenic edema is a mixture of increased water content and nerve fibers, and the nerve fibers extend through vasogenic edema. With vasogenic edema, the FA values are reduced, and the FA map cannot be used to determine whether a region includes a tumor or vasogenic edema. That is, even though the tractography of a tumor and vasogenic edema are distinctly different (an absence of nerve fibers versus a presence of nerve fibers), the standard diffusion MR approach is unable to distinguish a tumor and vasogenic edema. As a consequence, tractography based on the standard diffusion MR approach does not accurately map the tractography inside and/or near tumors in the brain, resulting in inaccurate data that might be insufficient for decision-making by a clinician such as a surgeon using a brain tractogram during a pre-surgical planning stage to identify regions to resect in the brain without damaging normal healthy nerve fibers.

In view of at least the foregoing, there is an unresolved need for an improved approach(s) for MR imaging-based tractography.

SUMMARY

Aspects described herein address the above-referenced problems and others. This summary introduces concepts that are described in more detail in the detailed description. It should not be used to identify essential features of the claimed subject matter, nor to limit the scope of the claimed subject matter.

In one aspect, a magnetic resonance (MR) imaging system includes a main magnet configured to generate a magnetic field, gradients coils configured to generate time varying gradient magnetic fields, and a radiofrequency (RF) transmit coil configured to generate RF signals. The MR imaging system further includes a controller configured to control the gradient coils and the RF transmit coil based on a first sequence that includes a pulse gradient spin echo (PGSE) acquisition and an oscillating gradient spin echo (OGSE) acquisition and an RF receive coil configured to receive first MR signals generated in response to the PGSE and OGSE acquisitions. The MR imaging system further includes an image reconstructor configured to process the first MR signals and generate a first apparent diffusion coefficient (ADC) map for the PGSE acquisition and a second ADC map for the OGSE acquisition. The MR imaging system further includes a processor configured to generate a seed point map based on the first and second ADC maps, wherein the seed point map visually distinguishes tumor and vasogenic edema.

In another aspect, a computer-implemented method includes controlling gradient coils and RF transmit coil of an MR imaging system based on a first sequence that includes a PGSE acquisition and an OGSE acquisition. The computer-implemented method further includes processing first MR signals generated in response to the PGSE and OGSE acquisitions and received by an RF receive coil of the MR imaging system to generate a first ADC map for the PGSE acquisition and a second ADC map for the OGSE acquisition. The computer-implemented method further includes generating a seed point map based on the first and second ADC maps, wherein the seed point map visually distinguishes tumor and vasogenic edema.

In another aspect, a computer readable medium is encoded with computer executable instructions. The computer executable instructions, when executed by a processor, cause the processor to control gradient coils and RF transmit coil of an MR imaging system based on a first sequence that includes a PGSE acquisition and an OGSE acquisition, process first MR signals generated in response to the PGSE and OGSE acquisitions and received by an RF receive coil of the MR imaging system to generate a first ADC map for the PGSE acquisition and a second ADC map for the OGSE acquisition, and generate a seed point map based on the first and second ADC maps, wherein the seed point map visually distinguishes tumor and vasogenic edema.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Embodiments of the present disclosure will now be described, by way of example, with reference to the figures, in which a system, a method and/or a computer readable medium with computer instructions improves tractography through processing MR data acquired via a predetermined set of acquisitions, including a PGSE time-dependent diffusion acquisition having a first diffusion time, an oscillating gradient spin echo (OGSE) time-dependent diffusion acquisition having a second, shorter diffusion time, and a T2-weighted SE acquisition without any diffusion gradient. The MR data from the PGSE and OGSE time-dependent diffusion acquisitions and the T2-weighted acquisition are used to generate apparent diffusion coefficient (ADC) maps and trace weighted maps, where the ADC and/or the trace weighted maps are used to identify nerve track seed points. The seed points are employed with existing MR tractography processes to grow nerve fibers and generate a tractogram. For example, the seed points can be employed in connection with FA maps and orientation distribution function (ODF) maps generated with MR data acquired using standard PGSE-based DTI acquisitions at different b-values to grow nerve fibers from the seed points and generate tractograms.

As described above, the standard diffusion MR approach for tractography (i.e., PGSE-based DTI and FA maps) is not capable of distinguishing between a tumor (solid, infiltrative, etc.) and vasogenic edema, and, thus, may not accurately map the tractography inside or near tumors in the brain, resulting in inaccurate data that might be insufficient for decision-making by a clinician such as a surgeon using a brain tractogram during a pre-surgical planning stage to identify regions to resect in the brain, without damaging normal healthy nerve fibers, and retaining normal brain function. Damaging normal healthy nerve fibers can result in loss of a bodily function. The tractography approach described herein is capable of visually distinguishing a tumor and vasogenic edema. As described in greater detail below, this is achieved through generating an ADC ratio map that is based on a ratio of ADC maps respectively from the PGSE and OGSE time-dependent diffusion acquisitions (and/or a trace weighted ratio map that is based on a ratio of trace weighted maps from the ADC maps) and identifying seed points therefrom. The approach described herein overcomes deficiencies of and improves existing MR tractography technology, at least with respect to accurately mapping the tractography inside or near tumors in the brain, such as generating nerve fibers extending through regions of vasogenic edema.

Figure 1:
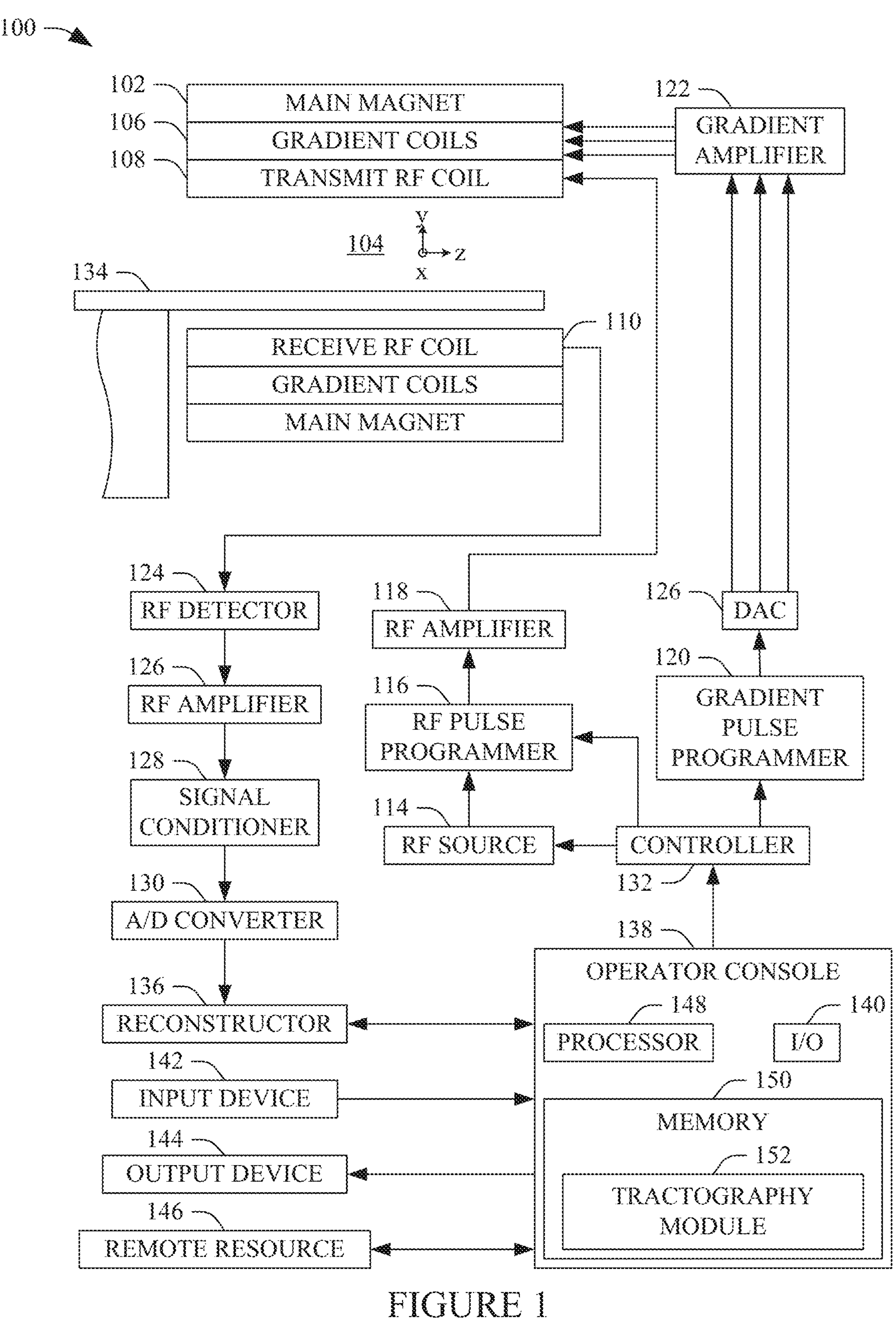
FIG. 1 schematically illustrates an example of an imaging system configured at least for magnetic resonance (MR) imaging, in accordance with an embodiment(s) herein.

Initially referring to FIG. 1, an imaging system 100 configured at least for magnetic resonance (MR) imaging is schematically illustrated. The imaging system 100 includes a main magnet 102. The main magnet 102 is configured to provide a substantially homogeneous, temporally constant main magnetic field $B_0$ in an examination region 104. Depending on the desired main magnetic field strength and the requirements of a particular application, various magnet technologies (e.g., superconducting, resistive, or permanent magnet technologies) and/or physical magnet configurations (e.g., solenoidal or open magnet configurations) have been implemented.

The imaging system 100 further includes gradient coils 106. The gradient coils 106 are configured to generate time varying magnetic gradient fields. The gradient coils 106 include an x-gradient coil for generating a gradient field along the x-direction, a y-gradient coil for generating a gradient field along the y-direction and a z-gradient coil for generating a gradient field along the z-direction. A function of the gradient coils 106 is to spatially encode the MR signal to differentiate signals from different locations within the body. The gradient coils 106 are also utilized for various techniques like diffusion imaging, perfusion imaging, functional imaging, elastography imaging, angiography imaging, etc. For diffusion imaging, the gradient coils 106 are configured to generate diffusion-sensitizing gradients that affect the image contrast.

The imaging system 100 further includes a transmit radiofrequency (RF) coil 108. The transmit RF coil 108 is configured to generate RF signals that excite and/or otherwise manipulate hydrogen and/or other magnetic resonant active nuclei in an object and/or subject in the examination region 104. The imaging system 100 further includes a receive RF coil 110. The receive RF coil 110 is configured to receive magnetic resonance (MR) signals generated by the excited nuclei in the examination region 104. The illustrated transmit RF coil 108 and receive RF coil 110 are volume or whole-body coils integrated in the imaging system 100.

In another example, the RF coil 108 is configured as the receive coil, and the RF coil 110 is configured as the transmit coil. In another instance, the transmit RF coil 108 and receive RF coil 110 are part of a same transmit-receive RF coil and a switch or the like is configured to switch between transmit and receive operations. In another instance, the transmit RF coil 108 and receive RF coil 110 are separate from the imaging system 100 and are installed in the imaging system 100 for use therewith to scan the object or subject. Other coils are contemplated herein. Examples include smaller volume coils configured for extremities such as the head, etc., surface coils, etc.

The imaging system 100 further includes an RF source 114. The RF source 114 is configured to generate an RF signal having a desired frequency (e.g., the Larmor frequency of the MR active nuclei under investigation). The imaging system 100 further includes an RF pulse programmer 116. The RF pulse programmer 116 is configured to establish a timing and/or a shape of the RF signal generated by the RF source 114. The imaging system 100 further includes an RF amplifier 118. The RF amplifier 118 is configured to amplify the shaped RF signal to levels required by the transmit RF coil 108 for exciting nuclei in the object or subject in the examination region 104.

The imaging system 100 further includes a gradient pulse programmer 120. The gradient pulse programmer 120 is configured to establish a timing, a strength and/or a shape of the time varying magnetic fields that are generated by the gradient coils 106 during a scan of an object and/or subject. The imaging system 100 further includes a gradient amplifier 122. The gradient amplifier 122 is configured to amplify the time varying magnetic fields to levels required by the respective gradient coils 106. The gradient amplifier 122 includes an independent power amplifier for each of the gradient coils 106, including the x-gradient coil, the y-direction and the z-gradient coil. In one example, the x- and y-gradient coils respectively include a saddle (Golay) coil and the z-gradient coil includes a circular (Maxwell) coil.

A controller 132 controls the RF source 114, the RF pulse programmer 116 and the gradient pulse programmer 120. The RF pulse programmer 116 and the gradient pulse programmer 120 respectively control the RF amplifier 118 and the gradient amplifier 122 based on an imaging technique being employed for a scan of an object or subject. As briefly discussed above, examples of different imaging techniques include diffusion imaging, perfusion imaging, functional imaging, elastography imaging, angiography imaging, etc., including a diffusion based tractography acquisition. As described in greater detail below, the diffusion based tractography acquisition includes a PGSE time-dependent diffusion acquisition having a longer diffusion time, an OGSE time-dependent diffusion acquisition having a shorter diffusion time, both time-dependent diffusion acquisitions having multiple diffusion encoding directions and a same b-value, a T2-weighted SE acquisition without any diffusion gradient, and a standard PGSE-based DTI acquisition with multiple diffusion encoding directions and one or more different b-values greater than zero.

The imaging system 100 further includes an RF detector 124. The RF detector 124 is configured to receive an analog MR signal generated by the RF receive coil 110 during a data acquisition window having a given timing and length. The imaging system 100 further includes an RF amplifier 126. The RF amplifier 126 is configured to amplify the received analog MR signal. The imaging system 100 further includes a signal conditioner 128. The signal conditioner 128 is configured to condition the amplified analog MR signal, e.g., demodulate, filter, etc., the amplified MR signal. The imaging system 100 further includes an analog-to-digital (A/D) converter 130. The A/D converter 130 is configured to digitize the conditioned analog MR signal, i.e., convert the conditioned analog MR signal into a digital MR signal.

The imaging system 100 further includes a subject/object support 134. The subject/object support 134 includes a tabletop moveably coupled to a frame/base. In one instance, the tabletop is slidably coupled to the frame/base via a bearing or the like, and a drive system (not visible) including a controller, a motor, a lead screw, and a nut (or other drive system) translates the tabletop along the frame/base into and out of the examination region 104. The tabletop is configured to support an object or subject in the examination region 104 for loading, scanning, and/or unloading the subject or object. A table controller (not visible) controls the drive system.

The imaging system 100 further includes a reconstructor 136. The reconstructor 136 is configured to reconstruct the digitized MR signals and generate individual axial (2-D) images and/or volumetric (3-D) image data. The MR signals include encoded imaging data (k-space), which is transformed by the image reconstruction algorithm using a Fourier transform and/or other algorithm. The 2-D images and/or the 3-D image data can be visually presented via a display monitor, filmer, etc. As described in greater detail below, for the diffusion based tractography technique, the reconstructor 136 is configured to process the MR signals acquired for the tractography acquisitions and generate ADC maps, trace weighted maps, FA maps, ODF maps, etc.

The imaging system 100 further includes a computing system 138. The computing system 138 serves as an operator console of the imaging system 100. The computing system 138 includes a computer, a workstation, etc. The computing system 138 includes input/output (I/O) 140. The computing system 138 is in communication with the reconstructor 136 through the I/O 140 and/or otherwise. An input device 142 includes a keyboard, mouse, touchscreen, microphone, etc. The input device 142 is in communication with the computing system 138 through the I/O 140 and/or otherwise. An output device 144 includes a human readable device such as a display monitor or the like. The output device 144 is in communication with the computing system 138 through the I/O 140 and/or otherwise.

A remote resource 146 includes one or more of a server, a workstation, a Radiology Information System (RIS), a Hospital Information System (HIS), an electronic medical record (EMR), a Picture Archiving and Communications System (PACS), one or more other MR scanners, cloud processing resources (which includes shared remote data storage and/or computing power, including processing resources distributed over multiple locations/data centers), etc. The remote resource 146 is in communication with the computing system 138 through the I/O 140 and/or otherwise. Images can be transferred therebetween and stored via Digital Imaging and Communications in Medicine (DICOM), etc., and other data can be transferred via Health Level Seven (HL7), etc.

The computing system 138 further includes at least one processor 148 such as a microprocessor (μP), a central processing unit (CPU), graphics processing unit (GPU), etc., and a computer readable medium 150 ("MEMORY"), which includes non-transitory medium and excludes transitory medium (signals, carrier waves, and the like). The computer readable medium 150 at least includes a tractography module 152. The at least one processor 148 is configured to provide control singles to the controller 132 to control the RF source 114, the RF pulse programmer 116 and the gradient pulse programmer 120, e.g., for a set of sequence for acquiring data to determine tractography. As described in greater detail below, for the diffusion based tractography technique, the tractography module 152 includes application software and one or more algorithms configured to process ADC maps, trace weighted maps, FA maps, ODF maps, user input seed points, etc. and produce tractograms that visually show nerve fibers in the brain, including nerve fibers extending through regions of vasogenic edema.

Figure 2:
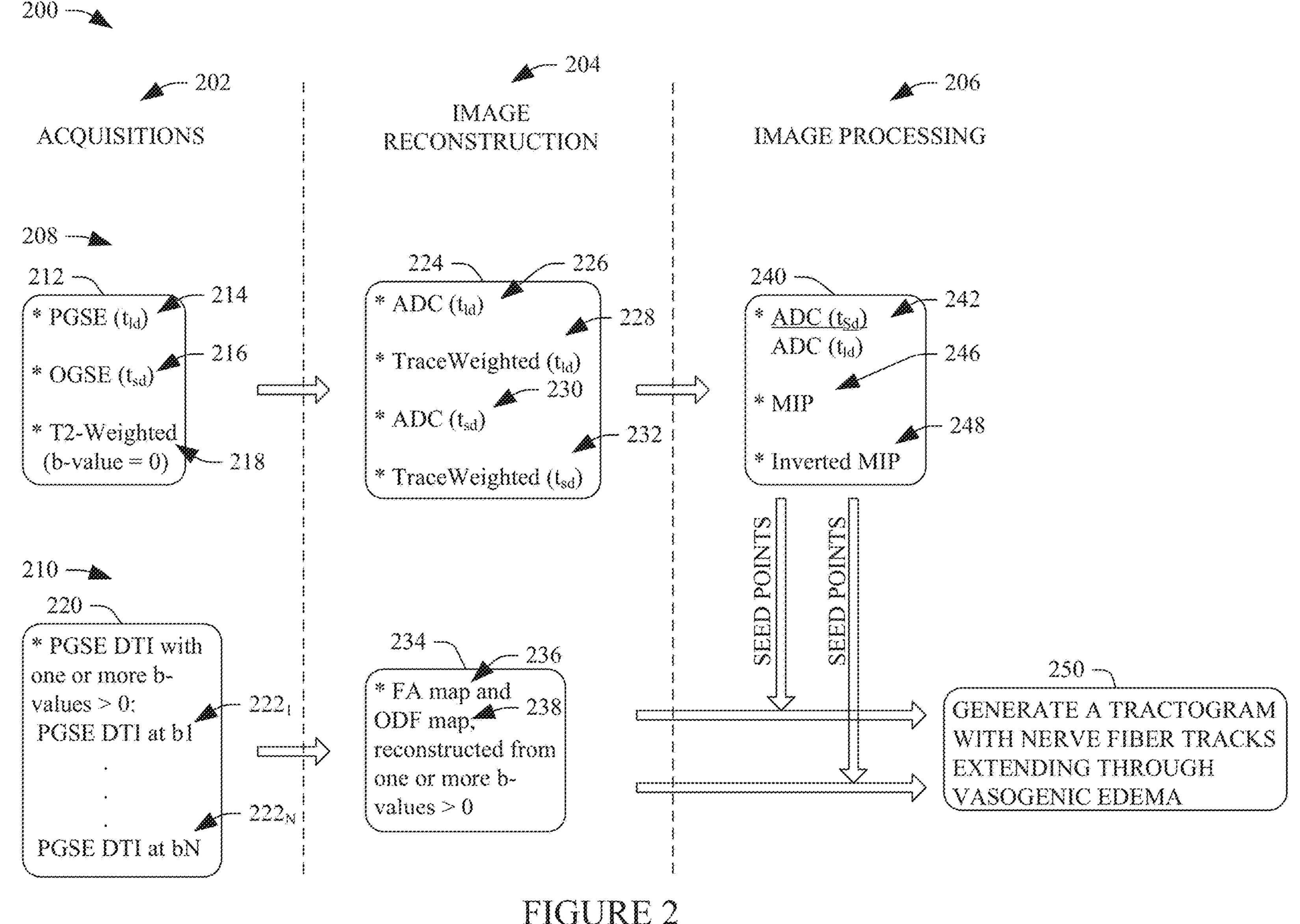
FIG. 2 diagrammatically illustrates an example tractography approach, in accordance with an embodiment(s) herein.

FIG. 2 diagrammatically illustrates an example flow diagram 200 of the tractography approach described herein. The flow diagram 200 includes an acquisition section 202, an image reconstruction section 204, and an image processing section 206. The flow diagram 200 further includes two data pipelines, a first data pipeline 208 and a second data pipeline 210. Both of the data pipelines 208 and 210 extend across the acquisition section 202, the image reconstruction section 204, and the image processing section 206. The first data pipeline 208 provides information for identifying nerve fiber seed points, including seed points for nerve fibers extending through vasogenic edema, and the second data pipeline 210 generates tractograms based on the identified nerve fiber seed points. Whereas the first data pipeline 208 includes new and/or improved processing, the second data pipeline 210 can include standard and/or other processing for generating tractograms.

For the first data pipeline 208, the acquisition section 202 includes multiple acquisitions 212. The multiple acquisitions include a PGSE acquisition with a longer diffusion time, PGSE ($t_{ld}$) 214. The multiple acquisitions 212 further include an OGSE acquisition with a shorter diffusion time, OGSE ($t_{sd}$) 216. The shorter diffusion time ($t_{sd}$) is shorter than the longer diffusion time ($t_{ld}$). The diffusion time corresponds to the amount of time during which water molecules diffuse before a measurement is recorded. The multiple acquisitions 212 further include a T2-weighted acquisition with no diffusion gradient (b-value=0) 218. For the second data pipeline 210, the acquisition section 202 also includes multiple acquisitions 220. In this example, the multiple acquisitions 220 include a PGSE-based DTI acquisition with one or more different b-values greater than zero, including a PGSE DTI at b1 $\mathbf{222}_1$, . . . , and a PGSE DTI at bN $\mathbf{222}_N$ (where N is an integer equal to or greater than one).

For the first data pipeline 208, the reconstruction section 204 includes multiple reconstructions 224. The multiple reconstructions 224 include an ADC map for the first diffusion time, ADC($t_{ld}$) 226, a trace weighted map for the first diffusion time, TraceWeighted($t_{ld}$) 228, an ADC map for the second diffusion time, ADC($t_{sd}$) 230, and a trace weighted map for the second diffusion time, TraceWeighted ($t_{sd}$) 232. For the second data pipeline 210, the reconstruction section 204 includes a reconstruction 234. The reconstructions 234 includes an FA map 236 and an ODF map 238. The FA map 236 and the ODF map 238 can be determined by using the data with one or more b-values greater than zero, based on standard and/or other approaches. For example, the ODF map can be determined based on a degree of spherical harmonics determined from the DTI signals.

For the first data pipeline 208, the imaging processing section 206 includes multiple image processing algorithms 240. The multiple image processing algorithms 240 include an algorithm to determine an ADC ratio map based on a ratio of the ADC($t_{sd}$) map to the ADC($t_{ld}$) map, or ADC($t_{sd}$)/ADC ($t_{ld}$) 242. The multiple image processing algorithms 240 further include an algorithm to determine a maximum projection intensity (MIP) of the ADC ratio map, or MIP 246. The multiple image processing algorithms 240 further include an algorithm to determine an inverse of the MIP map, or inverted MIP 248. For the second data pipeline 210, the imaging processing section 240 includes a tractography algorithms 250. The tractography algorithm 250 is configured to generate a tractogram, based on the respective FA map 236 and ODF map 238 and a set of user identified seeds points determined from the inverted MIP 248. The tractography algorithms 250 grow nerve fiber tracts from the seed points using standard and/or other approaches. As discussed herein, the tractograms will include nerve fibers extending through vasogenic edema.

Figure 3:
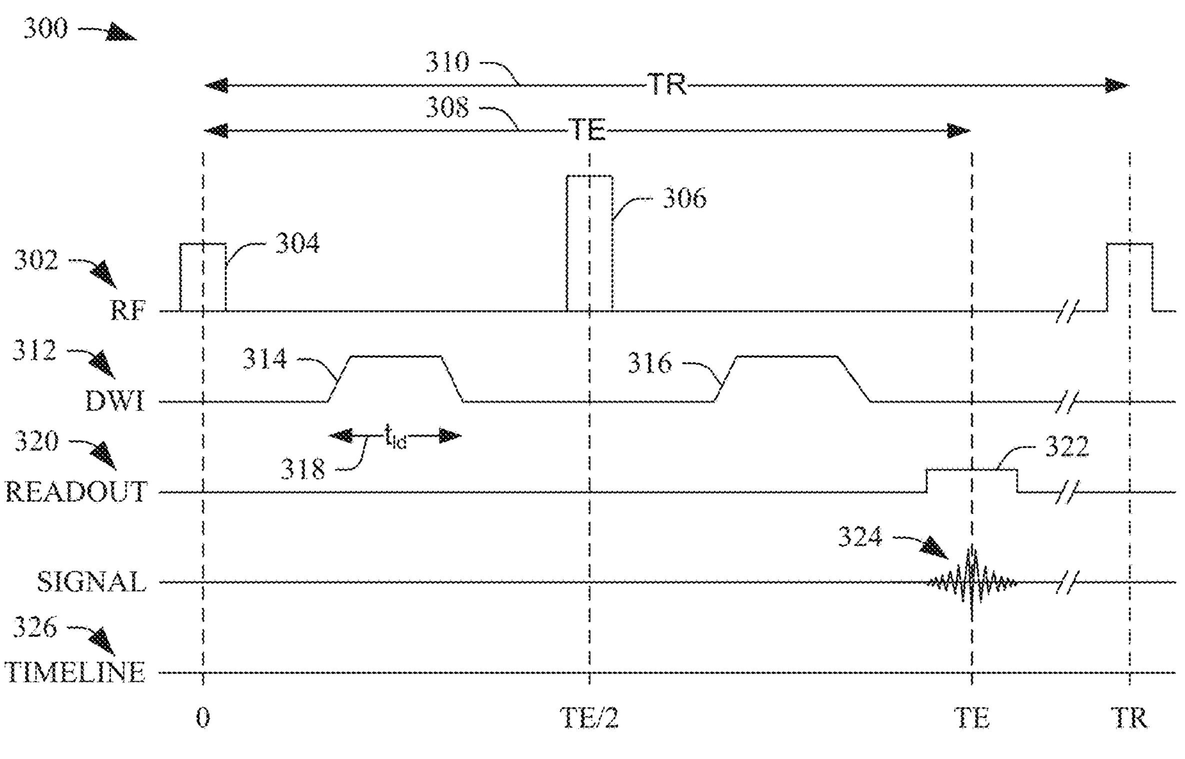
FIG. 3 schematically illustrates an example sequence diagram for a PGSE based diffusion sequence, in accordance with an embodiment(s) herein.

FIG. 3 diagrammatically illustrates a sequence diagram 300 for the PGSE based time-dependent diffusion acquisition PGSE ($t_{ld}$) 214 (FIG. 2). The sequence diagram 300 includes an RF sequence 302 with a ninety-degree (90°) excitation pulse 304 at t=0 and a one hundred and eighty degree (180°) refocusing pulse 306 at TE/2. A suitable value of TE 308 is a value in a range of 30<TE<160 milliseconds (ms). A suitable value of TR 310 is a value in a range of 1000 ms<TR<20000 ms. The sequence diagram 300 further includes a DWI sequence 312 with a first single gradient pulse 314 before the refocusing pulse 306 and a second signal gradient pulse 316 after the refocusing pulse 306. A suitable longer diffusion time $t_{ld}$ 318 is a value in a range of 20 ms<$t_d$<120 ms. The sequence diagram 300 further shows a readout sequence 320 with a data acquisition (DAQ) pulse 322. For reference, FIG. 3 also shows an echo signal 324 and a timeline 326. For sake of brevity and clarity, FIG. 3 does not show x, y and z gradient pulse sequences, however, multiple diffusion encoding directions are utilized. In addition, FIG. 3 does not show gradients for k-space imaging.

Figure 4:
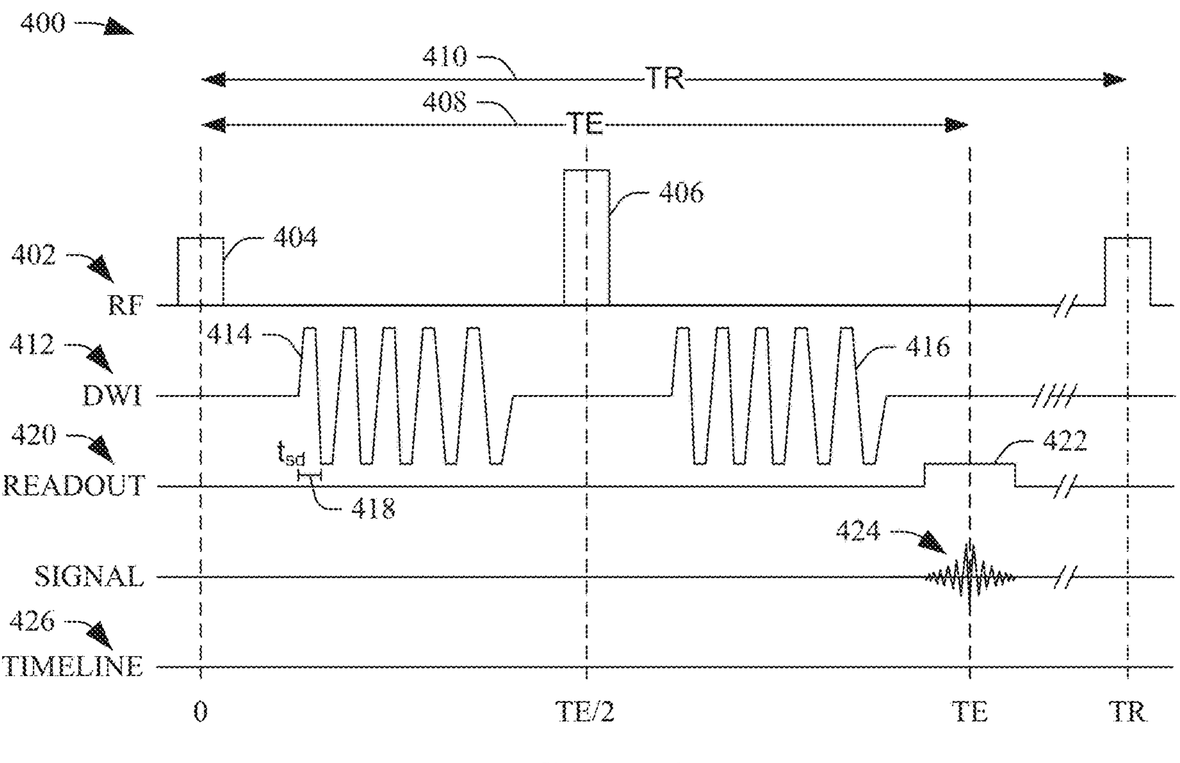
FIG. 4 schematically illustrates an example sequence diagram for an OGSE based diffusion sequence, in accordance with an embodiment(s) herein.

FIG. 4 diagrammatically illustrates a sequence diagram 400 for an OGSE based time-dependent diffusion acquisition OGSE ($t_{sd}$) 216 (FIG. 2). The sequence diagram 400 includes an RF sequence 402 with a 90° excitation pulse 404 at t=0 and a 180° refocusing pulse 406 at TE/2. A suitable value of TE 408 is a value in a range of 30 ms<TE<160 milliseconds (ms). A suitable value of TR 410 is a value in a range of 1000 ms<TR<20000 ms. The sequence diagram 400 further includes a DWI sequence 412 with a first oscillating gradient pulse 414 before the refocusing pulse 406 and a second oscillating gradient pulse 416 after the refocusing pulse 406. A suitable shorter diffusion time $t_{SD}$ 418 is a value in a range of 0.001 ms<$t_{sd}$<10 ms. The sequence diagram 400 further shows a readout sequence 420 with a DAQ pulse 422. For reference, FIG. 4 also shows an echo signal 424 and a timeline 426. For sake of brevity and clarity, FIG. 4 does not show x, y and z gradient pulse sequences, however, multiple diffusion encoding directions are utilized. In addition, FIG. 4 does not show gradients for k-space imaging.

As discussed in connection with FIG. 2, other acquisition sequences for the tractography approach described herein include the T2-weighted (b-value=0) 218 acquisition, and the PGSE DTI at b1 $\mathbf{222}_1$, . . . , PGSE DTI at bN $\mathbf{222}_N$ acquisitions, with multiple diffusion encoding directions and one or more non-zero b-values. Suitable b-values include a value in a range ≥800 s/mm$^2$. Standard and/or other sequences can be used for the T2-weighted (b-value=0) 218 acquisition and the PGSE DTI at b1 $\mathbf{222}_1$, . . . , PGSE DTI at bN $\mathbf{222}_N$ acquisitions, FIG. 5 visually depicts an ADC map 500 for the MR data acquired in response to the PGSE based time-dependent diffusion acquisition, PGSE ($t_{ld}$) 214 (FIG. 2). In general, the ADC map 500 is an image in which pixel values correspond to the apparent diffusion coefficient of water molecules in a given tissue, which shows how the molecules disperse and traverse within the tissue. The diffusion time corresponds to the amount of time during which water molecules diffuse before a measurement is recorded.

The calculation of the ADC map 500 can be based on the standard and/or other approach. For example, in one instance the ADC values for the ADC map 500 are determined based on EQUATIONS 1 and 2:

$$S = S_0 e^{(-b * ADC(t_{ld}))}, \quad \text{EQUATION 1}$$

where S represents the MR signal for the PGSE based time-dependent diffusion acquisition, PGSE ($t_{ld}$) 214, $S_0$ represents the MR signal without any diffusion gradient (i.e., b-value=0), b represents the b-value, and ADC($t_{ld}$) represents the ADC at the longer diffusion time $t_{ld}$. $S_0$ can be determined from the MR data acquired for the T2-weighted sequence 218, which does not include any diffusion gradient, i.e., b-value=0. The ADC($t_{ld}$) can then be determined based on EQUATION 2:

$$ADC(t_{ld}) = -\ln\left(\frac{S}{S_0}\right) \Big/ b. \quad \text{EQUATION 2}$$

In this example, the ADC map 500 includes lesions in regions of interest (ROI) 502, which include a first region 504 that contains contrast-enhanced biopsy-confirmed solid tumor, a second region 506 that contains non-enhancing lesions that may be infiltrative tumor, and a third region 508 that contains non-enhancing lesions that may be vasogenic edema. However, from the ADC map 500, the contents of the regions 506 and 508 are not visually distinguishable from each other. As such, a clinician reading the ADC map 500 would not be able to decisively identify the contents of each of the regions 506 and 508 from the ADC map 500. That is, the clinician, from the ADC map 500, could not decisively determine that the second region 506 contains infiltrative tumor, and the third region 508 contains vasogenic edema.

Figures 5, 6:
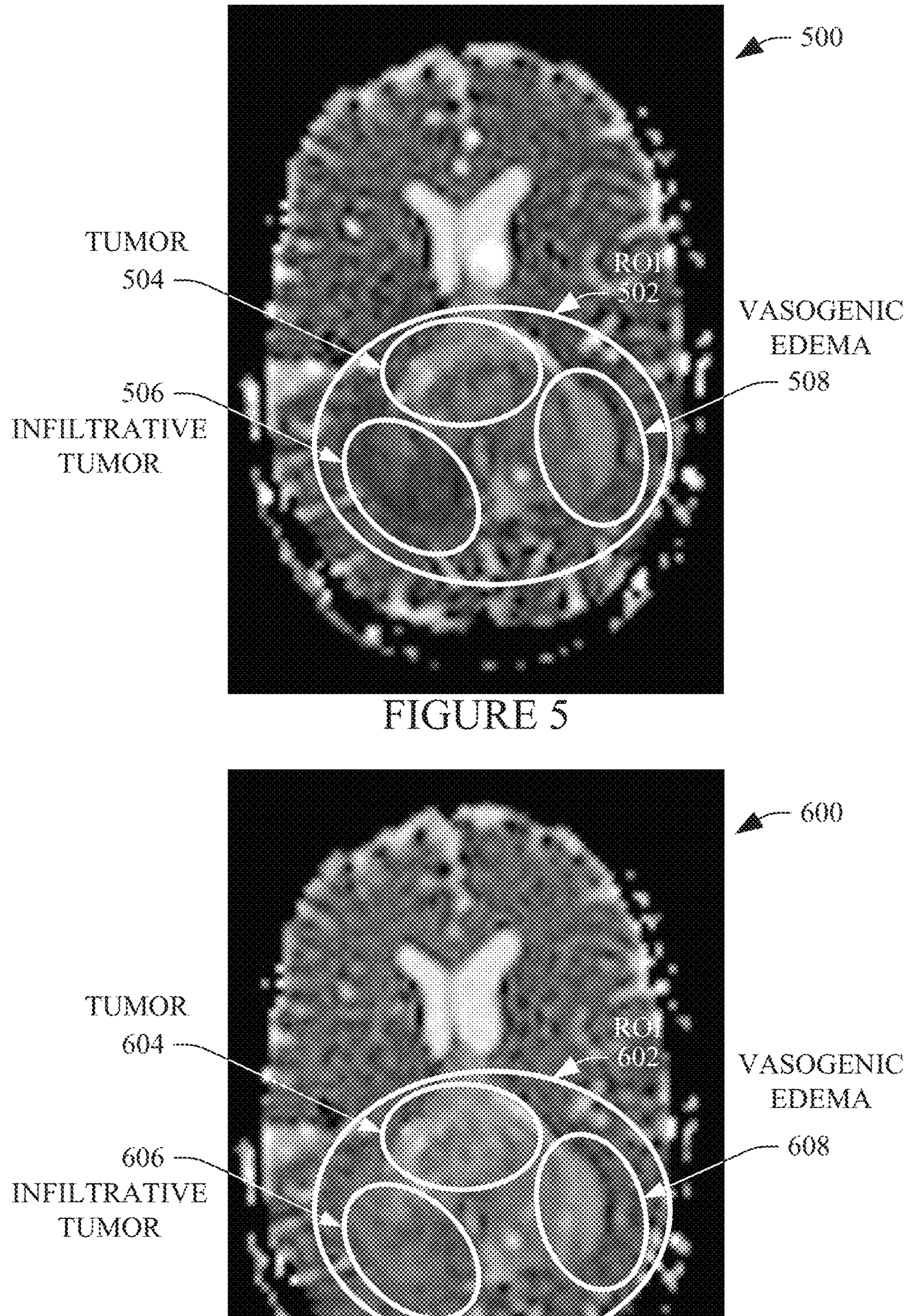
FIG. 5 depicts an ADC map generated based on the MR data acquired for the PGSE based dependent diffusion sequence of FIG. 3, in accordance with an embodiment(s) herein.
FIG. 6 depicts an ADC map generated based on the MR data acquired for the OGSE based dependent diffusion sequence of FIG. 4, in accordance with an embodiment(s) herein.

FIG. 6 visually depicts an ADC map 600 the MR data acquired in response to the OGSE based time-dependent diffusion acquisition, OGSE ($t_{sd}$) 216 (FIG. 2). Likewise, the ADC map 600 is an image in which pixel values correspond to the apparent diffusion coefficient of water molecules in a given tissue, which shows how the molecules disperse and traverse within the tissue, and, again, the diffusion time corresponds to the amount of time during which water molecules diffuse before a measurement it recorded.

Similarly, the calculation of the ADC map 600 can be based on the standard and/or other approach. For example, in one instance the ADC values for the ADC map 600 are determined based on EQUATIONS 3 and 4:

$$S = S_0 e^{(-b * ADC(t_{sd}))}, \quad \text{EQUATION 3}$$

where S represents the measured MR signal for the OGSE based time-dependent diffusion acquisition, OGSE ($t_{sd}$) 216, $S_0$ represents the MR signal without any diffusion gradient, b represents the b-value, and ADC($t_{sd}$) represents the ADC for the short diffusion time $t_{sd}$. $S_0$ can be determined from the MR data acquired for the T2-weighted sequence T2-weighted (b-value=0) 218, which does not include any diffusion gradient, i.e., b=0. The ADC($t_{sd}$) can then be determined based on EQUATION 4:

$$ADC(t_{sd}) = -\ln\left(\frac{S}{S_0}\right) \Big/ b. \quad \text{EQUATION 4}$$

In this example, the ADC map 600 includes a region of interest (ROI) 602, which includes a first region 604 that contains contrast-enhanced biopsy-confirmed solid tumor, a second region 606 that contains non-enhancing lesions that may be infiltrative tumor, and a third region 608 that contains non-enhancing lesions that may be vasogenic edema. The regions 604, 606 and 608 correspond to the regions 504, 506 and 508 in FIG. 5. Similar to the ADC map 500 of FIG. 5, in the ADC map 600 of FIG. 6 the contents of the individual regions 604, 606 and 608 are not visually distinguishable from each other. As such, a clinician reading the ADC map 600 would not be able to decisively identify the contents of each of the regions 604, 606 and 608 from the ADC map 600. That is, the clinician, from the ADC map 600, could not decisively determine that the first region 604 contains tumor, the second region 606 contains infiltrative tumor, and the third region 608 contains vasogenic edema.

Figures 7, 8:
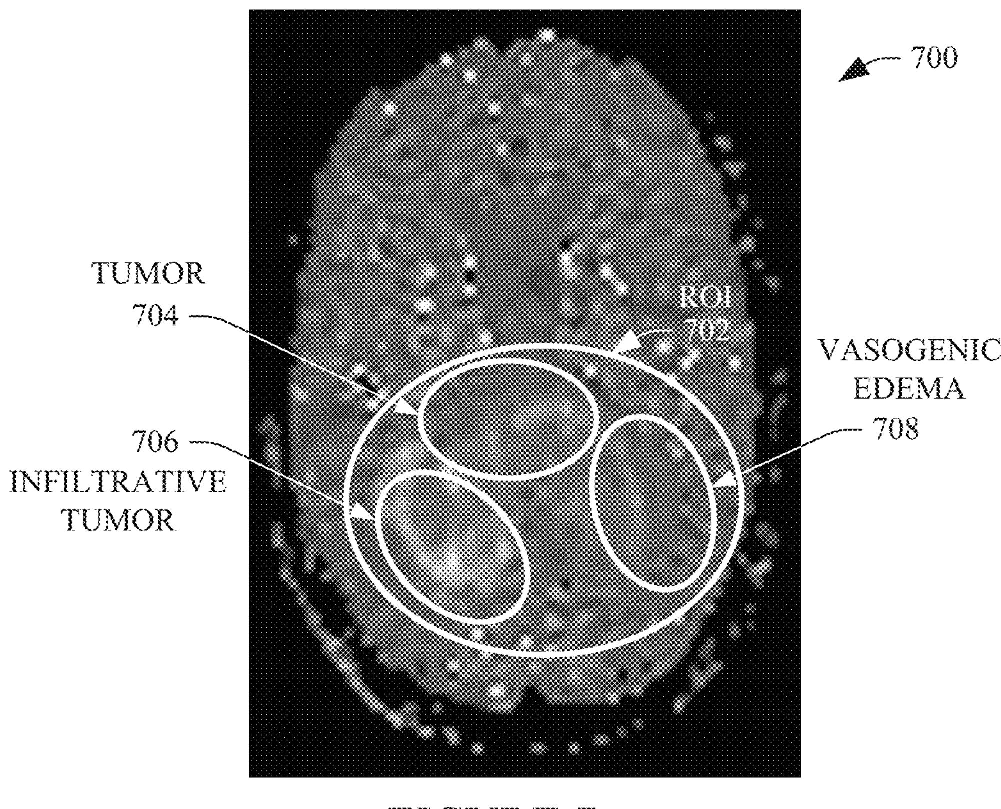
FIG. 7 depicts an ADC ratio map generated based on the ADC map of FIG. 5 and the ADC map of FIG. 6, in accordance with an embodiment(s) herein.
FIG. 8 depicts an MIP of a portion of the ADC map of FIG. 7, in accordance with an embodiment(s) herein.

With reference to FIG. 7, and continuing references to FIGS. 5 and 6, an ADC ratio map 700 determined based on the ADC map 500 of FIG. 5 and the ADC map 600 of FIG. 6 is visually illustrated. In one instance, the ADC ratio map 700 is determined based on a ratio of the ADC map 500 to the ADC map 600 (ADC($t_{sd}$)/ADC($t_{ld}$) 242 in FIG. 2), as shown in EQUATION 5:

$$ADC = \frac{ADC(t_{sd})}{ADC(t_{ld})}, \quad \text{EQUATION 5}$$

where ADC($t_{sd}$) is determined from EQUATION 4 and ADC($t_{ld}$) is determined from EQUATION 2. The ratio ADC($t_{sd}$)/ADC($t_{ld}$) is discussed in detail in Zhu et al., "Revealing tumor microstructure with oscillating diffusion encoding MRI in pre-surgical and post-treatment glioma patients," Magn Reson Med. 2023; 90:1789-1801.

In this example, the ADC ratio map 700 includes a region of interest (ROI) 702, which includes a first region 704 that contains contrast-enhanced biopsy-confirmed solid tumor, a second region 706 that contains non-enhancing lesions that may be infiltrative tumor, and a third region 708 that contains non-enhancing lesions that may be vasogenic edema. The regions 704, 706 and 708 correspond to the regions 504, 506 and 508 in the ADC map 500 in FIG. 5 and the regions 604, 606 and 608 in the ADC map 600 in FIG. 6. However, in the ADC ratio map 700 of FIG. 7 the contents of the individual regions 704, 706 and 708 are visually distinguishable from each other. As a result, a clinician reading the ADC ratio map image 700 would be able to identify the contents of each of the regions 704, 706 and 708 from the ADC ratio map 700. That is, the clinician, from the ADC ratio map 700, could determine that the first region 704 contains contrast-enhanced biopsy-confirmed solid tumor, the second region 706 contains non-enhancing infiltrative tumor, and the third region 708 contains non-enhancing vasogenic edema.

In general, the ADC values for regions of healthy white and/or grey matter (regions outside of 502 and 602) in the ADC map 500 and the ADC map 600 will be similar (e.g., approximately one) such that their ratio in the ADC ratio map 700 will be approximately one. Vasogenic edema regions 508 and 608 in FIGS. 5 and 6 include water and white and/or grey matter, and the ADC values for the regions 508 and 608 in the ADC map 500 and 600 will be slightly different than the ADC values of white and/or grey matter in the ADC map 500 and the ADC map 600 such that their ratio in the ADC ratio map 700 will be close to one. However, the ADC values for tumor tissue increase with shorter diffusion time and decrease with longer diffusion time. As such, the ratio of the ADC values for the regions 504, 506, 604 and 606 in FIGS. 5 and 6 will produce larger values. In other words, relative to the white and/or grey matter, the ADC ratio values in FIG. 7 for tumor will appear hyper-intensity and the ADC ratio values in FIG. 7 for vasogenic edema will appear iso-intensity. As such, the regions 704 and 706 including tumor in the ADC ratio map 700 of FIG. 7 are visually distinguishable from the region 708 including vasogenic edema in the ADC ratio map 700 of FIG. 7.

FIG. 8 visually illustrates an example MIP image 800 (corresponding to the MIP 246 in FIG. 2) generated for the ADC ratio map 700 in FIG. 7, i.e., from a stack of ADCs created for multiple MR images of the acquisition. In the MIP image 800, darker (e.g., black) pixels 802 correspond to healthy white, gray matter, and/or regions of vasogenic edema such as the region 508 in the ADC map 500 of FIG. 5, the region 608 in the ADC map 600 of FIG. 6, and the region 708 in the ADC ratio map 700 of FIG. 7; brighter intensity pixels 804 (relative to the pixels 802) correspond to regions of tumor and its infiltration such as the regions 504 and 506 in the ADC map 500 of FIG. 5, the regions 604 and 606 in the ADC map 600 of FIG. 6, and the regions 704 and 706 in the ADC ratio map 700 of FIG. 7. In the inverted MIP image (corresponding to inverted MIP 248 in FIG. 2), the intensities of the pixels in MIP image 800 in FIG. 8 are inverted, i.e., higher intensity pixels become lower intensity pixels and lower intensity pixels become higher intensity. As such, the pixels 804 corresponding to regions of tumor and its infiltration will be black or close to black and the pixels 806 corresponding to vasogenic edema will be brighter, relative to the pixels 804 corresponding to regions of tumor and its infiltration.

In one instance the ADC ratio map 700 of FIG. 7 is used to identify nerve seed points, including nerve seed points of nerve fibers extending through vasogenic edema. In another instance, the ADC ratio map 700 is processed to generate an MIP image. This corresponds to the MIP 246 in FIG. 2. The MIP 246 can then be used to identify nerve seed points, including nerve seed points of nerve fibers extending through vasogenic edema. In another instance, the MIP image can be processed to generate an inverted MIP image. This corresponds to the inverted MIP 248 in FIG. 2. The inverted MIP 248 can then be used to identify nerve seed points, including nerve seed points of nerve fibers extending through vasogenic edema. In general, the user of the tractography software can utilize the ADC ratio map 700 of FIG. 7, the MIP 246, and/or the inverted MIP to identify seed points for vasogenic edema. This may include using an input device such as a mouse to "click" on a point (i.e., place a seed point) for a region of vasogenic edema at which a nerve fiber will be grown. Once the seed points are placed, the tractography module 252 (FIG. 2) can process the FA map 236 and the ODF map 238 and grow nerve fiber tracts from the seed points using standard and/or other approaches to produce tractograms that will include nerve fibers extending through vasogenic edema.

The trace weighted maps TraceWeighted($t_{ld}$) 228 and TraceWeighted($t_{sd}$) 232 are also generated in the image reconstruction section 204. Similar to the ADC maps, the trace weighted maps can be generated based on standard approaches. For example, in one instance a trace weighted map can be determined from the PGSE acquisition PGSE ($t_{ld}$) 214 of FIG. 2 based on EQUATION 6:

$$TraceWeighted(t_{ld}) = e^{(-b*ADC(t_{ld}))}, \qquad \text{EQUATION 6}$$

using the ADC($t_{ld}$) determined from EQUATION 2, and a trace weighted map can be determined from the OGSE acquisition OGSE ($t_{sd}$) 216 of FIG. 2 based on EQUATION 7:

$$TraceWeighted(t_{sd}) = e^{(-b*ADC(t_{sd}))}, \qquad \text{EQUATION 7}$$

using the ADC($t_{sd}$) determined from EQUATION 4. A trace weighted ratio map can then be determined based the trace weighted image for the PGSE acquisition PGSE ($t_{ld}$) 214 and the trace weighted image for the OGSE acquisition OGSE ($t_{sd}$) 216 as shown in EQUATION 8:

$$TraceWeighted = \frac{TraceWeighted(t_{sd})}{TraceWeighted(t_{ld})}. \qquad \text{EQUATION 8}$$

In this instance, the MIP image 800 of FIG. 8 can be generated based on the ADC ratio map 700 of FIG. 7 and/or the trace weighted ratio map, and an inverted MIP map can be generated based on the MIP map 800 of FIG. 8 as discussed above and/or the MIP map of the trace weighted ratio map.

Figure 9:
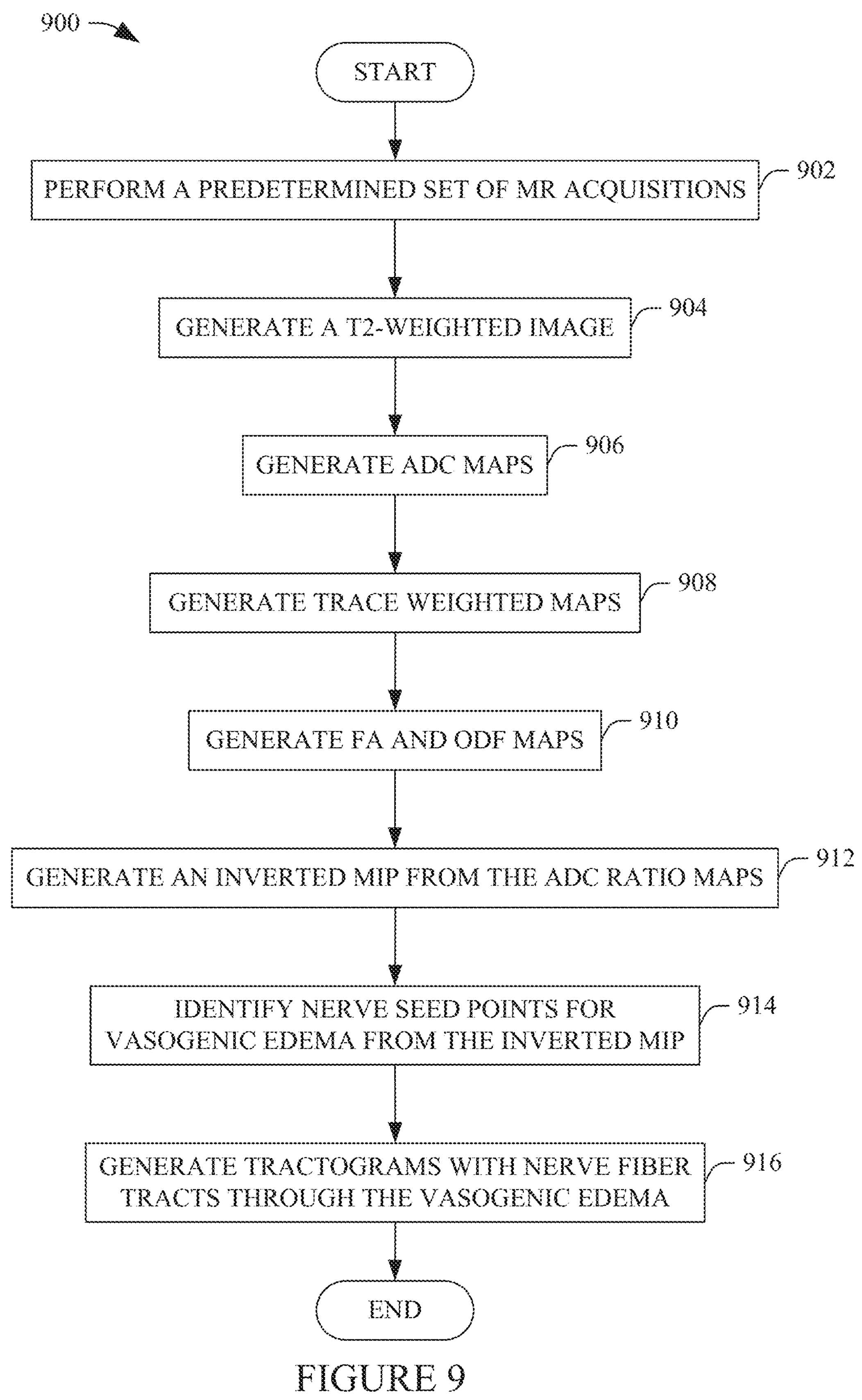
FIG. 9 illustrates a non-limiting example of a flow chart for a computer-implemented tractography method using ADC ratio maps to identify nerve seed points for vasogenic edema, in accordance with an embodiment(s) herein.

FIG. 9 illustrates a non-limiting example of a flow chart for a computer-implemented tractography method using ADC maps to identify nerve seed points for vasogenic edema. It is to be appreciated that the ordering of the acts in the method is not limiting. As such, other orderings are contemplated herein. In addition, one or more acts may be omitted, and/or one or more additional acts may be included.

At 902, MR data based on a predetermined set of sequences is acquired, as described herein and/or otherwise. For example, in one instance MR data is acquired for a first PGSE sequence with a longer diffusion time, a second PGSE sequence with a shorter diffusion time, a T2-weighted sequence, a PGSE DTI sequence at b1, . . . , and a PGSE DTI sequence at bN. As discussed herein, there is no particular order for the sequences. At 904, a T2-weighted image is generated for the T2-weighted sequence, as described herein and/or otherwise. As described herein, the b-value for the T2-weight sequence is zero. At 906, an ADC map is generated for the first PGSE sequence with the longer diffusion time using the T2-weighted image, and an ADC map is generated for the second PGSE sequence with the shorter diffusion time using the T2-weighted image, as described herein and/or otherwise. As discussed herein, a single b-value and multiple diffusion directions are utilized for both of the ADC images.

At 908, a trace weighted map is generated for the first PGSE sequence with the long diffusion time and a trace weighted map is generated for the second PGSE sequence with the short diffusion time, as described herein and/or otherwise. As discussed herein, the single b-value is utilized for both of the trace weighted maps. At 910, an FA map and an ODF map are generated from the MR data from the PGSE DTI sequence at b1, . . . , and an FA map and an ODF map are generated from the MR data from the PGSE DTI sequence at bN, as described herein and/or otherwise. For example, in one instance standard and/or approaches are utilized to generate the FA and ODF maps.

At 912, an inverted MIP map is generated based on the ADC ratio map for the first PGSE sequence and the ADC map for the second OGSE sequence, as described herein and/or otherwise. For example, in one instance an ADC ratio map is generated based on the ADC maps, an MIP of the ADC ratio map is determined, and an inverted MIP map is determined from the MIP of the ADC ratio map. At 914, the inverted MIP map is utilized to identify seed points, as described herein and/or otherwise. As discussed herein, regions of tumor are visually distinguishable from regions of vasogenic edema in the inverted MIP image. At 916, a tractography module generates tractograms by growing nerve fibers from the identified seed points, including nerve tracts through the regions of vasogenic edema, as described herein and/or otherwise.

Figure 10:
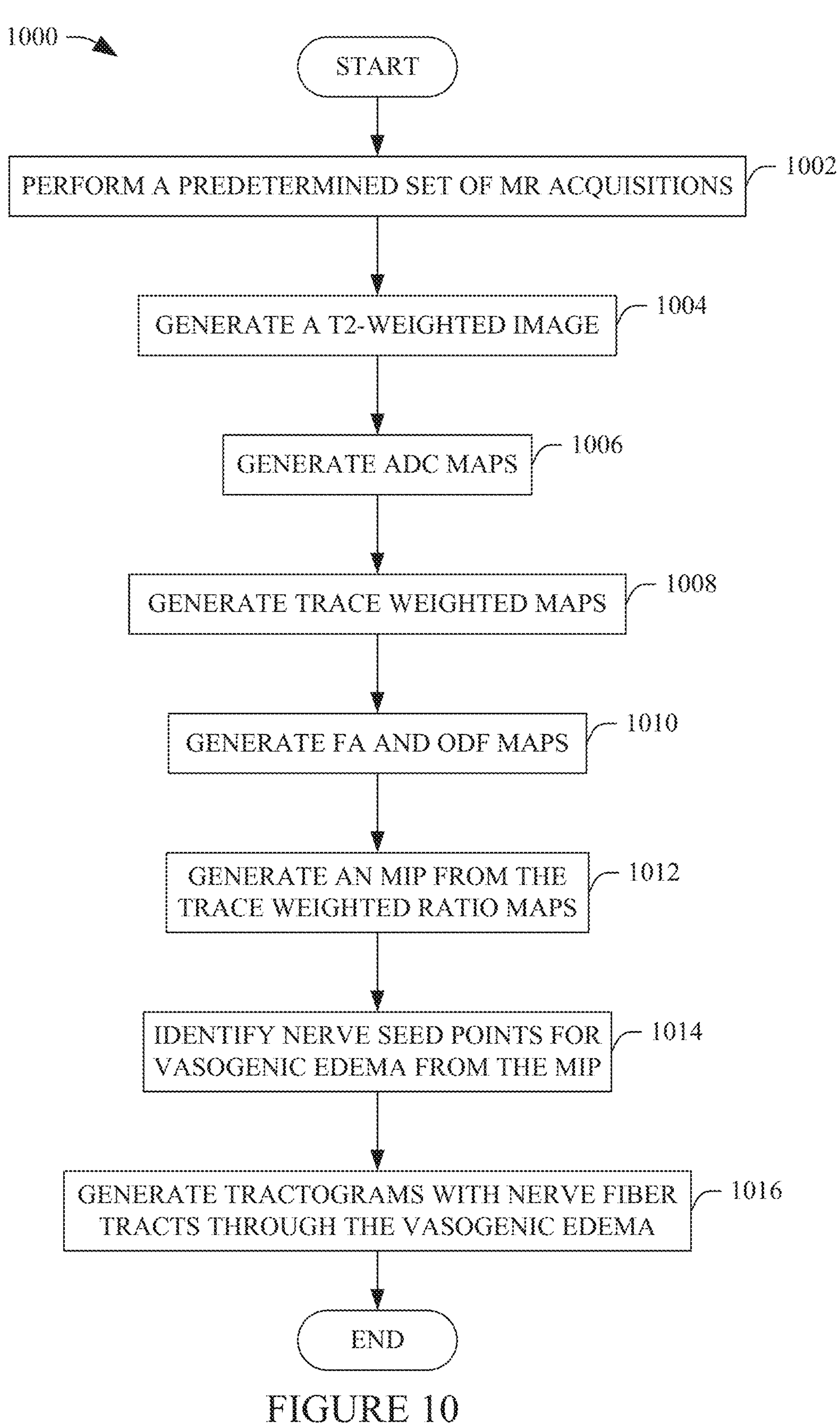
FIG. 10 illustrates another non-limiting example of a flow chart for a computer-implemented tractography method using trace weighted ratio maps to identify nerve seed points for vasogenic edema, in accordance with an embodiment(s) herein.

FIG. 10 illustrates a non-limiting example of a flow chart for another computer-implemented tractography method using trace weighted images to identify nerve seed points for vasogenic edema. It is to be appreciated that the ordering of the acts in the method is not limiting. As such, other orderings are contemplated herein. In addition, one or more acts may be omitted, and/or one or more additional acts may be included.

At 1002, MR data based on a predetermined set of sequences is acquired, as described herein and/or otherwise. For example, in one instance MR data is acquired for a first PGSE sequence with a longer diffusion time, a second PGSE sequence with a shorter time, a T2-weighted sequence, a PGSE DTI sequence at b1, . . . , and a PGSE DTI sequence at bN. As discussed herein, there is no particular order for the sequences. At 1004, a T2-weighted image is generated for the T2-weighted sequence, as described herein and/or otherwise. As described herein, the b-value for the T2-weight sequence is zero. At 1006, a trace weighted map is generated for the first PGSE sequence with the longer diffusion time using the T2-weighted image, and a trace weighted map is generated for the second PGSE sequence with the shorter diffusion time using the T2-weighted image, as described herein and/or otherwise. As discussed herein, a single b-value and multiple diffusion directed are utilized for both of the trace weighted images.

At 1008, a trace weighted map is generated for the first PGSE sequence with the longer diffusion time and a trace weighted map is generated for the second PGSE sequence with the shorter diffusion time, as described herein and/or otherwise. As discussed herein, the single b-value is utilized for both of the trace weighted maps. At 1010, an FA map and an ODF map are generated from the MR data from the PGSE DTI sequence at b1, . . . , and an FA map and an ODF map are generated from the MR data from the PGSE DTI sequence at bN, as described herein and/or otherwise. For example, in one instance standard and/or approaches are utilized to generate the FA and ODF maps.

At 1012, an MIP map is generated based on the trace weighted ratio map for the first PGSE sequence and the trace weighted map for the second OGSE sequence, as described herein and/or otherwise. For example, in one instance a trace weighted ratio map is generated based on the trace weighted maps, an MIP of the trace weighted ratio map is determined. At 1014, the MIP map is utilized to identify seed points, as described herein and/or otherwise. As discussed herein, regions of tumor and infiltrative tumor are visually distinguishable from regions of vasogenic edema in the MIP. At 1016, a tractography module generates tractograms by growing nerve fibers from the identified seed points, including nerve tracts through the regions of vasogenic edema, as described herein and/or otherwise.

The above method(s) can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms “software” and “firmware” are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions that require them, but this should not be taken to mean that the features in the dependent claims are mutually exclusive.

What is claimed is:

1. A magnetic resonance (MR) imaging system, comprising:

a main magnet configured to generate a magnetic field;

gradients coils configured to generate time varying gradient magnetic fields;

a radiofrequency (RF) transmit coil configured to generate RF signals;

a controller configured to control the gradient coils and the RF transmit coil based on a first sequence that includes a pulse gradient spin echo (PGSE) acquisition and an oscillating gradient spin echo (OGSE) acquisition;

an RF receive coil configured to receive first MR signals generated in response to the PGSE and OGSE acquisitions;

an image reconstructor configured to process the first MR signals and generate a first apparent diffusion coefficient (ADC) map for the PGSE acquisition and a second ADC map for the OGSE acquisition; and a processor configured to generate a seed point map based on the first and second ADC maps, wherein the seed point map visually distinguishes tumor and vasogenic edema.

2. The MR imaging system of claim 1, wherein the processor is further configured to generate a tractogram based on the seed points determined from the seed point map, wherein the tractogram includes a nerve fiber extending from the seed points through the vasogenic edema.

3. The MR imaging system of claim 1, wherein the PGSE has a first diffusion time, the OGSE has a second diffusion time, and the first diffusion time is longer than the second diffusion time.

4. The MR imaging system of claim 3, wherein the processor is further configured to generate an ADC ratio map of the OGSE ADC map to the PGSE ADC map.

5. The MR imaging system of claim 4, wherein the processor is further configured to generate a maximum intensity projection (MIP) image based on the ADC ratio map, and generate an inverted MIP image based on the MIP image, wherein the inverted MIP image depicts the vasogenic edema with first brightness pixels and the tumor with second brightness pixels, wherein the first brightness is brighter than the second brightness.

6. The MR imaging system of claim 4, wherein the processor is further configured to generate a first trace weighted map based on the first ADC map, and generate a second trace weighted map based on the second ADC map.

7. The MR imaging system of claim 6, wherein the processor is further configured to generate a trace weighted ratio map of the first trace weighted map and the second trace weighted map, generate an MIP image based on the trace weighted ratio map, and generate an MIP image based on the MIP image, wherein the MIP image depicts the vasogenic edema with first darkness pixels and the tumor with second darkness pixels, wherein the second darkness is brighter than the first darkness.

8. The MR imaging system of claim 1, wherein the controller is further configured to control the gradients coils and the RF transmit coil based on a second sequence that includes one PGSE diffusion tensor imaging (DTI) sequence with one or more different b-values greater than zero, and the receive coil configured to receive second MR signals generated by magnetically active nuclei in response to the one PGSE DTI sequence.

9. The MR imaging system of claim 8, wherein the image reconstructor is further configured to process the second MR signals and generate one fractional anisotropic (FA) map and one orientation distribution function (ODF) map, by using the PGSE DTI data with one or more b-values greater than zero.

10. The MR imaging system of claim 9, wherein the processor is further configured to generate a tractogram based on the FA map, the ODF map, and a user input indicative of one or more seed points determined from the seed point map.

11. A computer-implemented method, comprising:

controlling gradient coils and RF transmit coil of an MR imaging system based on a first sequence that includes a PGSE acquisition and an OGSE acquisition;

processing first MR signals generated in response to the PGSE and OGSE acquisitions and received by an RF receive coil of the MR imaging system to generate a first ADC map for the PGSE acquisition and a second ADC map for the OGSE acquisition; and generating a seed point map based on the first and second ADC maps, wherein the seed point map visually distinguishes tumor and vasogenic edema.

12. The computer-implemented method of claim 11, wherein the processor is further configured to generate a tractogram based on the seed points determined from the seed point map, and the tractogram includes a nerve fiber extending from the seed points through the vasogenic edema.

13. The computer-implemented method of claim 12, wherein the PGSE has a first diffusion time, the OGSE has a second diffusion time, the first diffusion time is longer than the second diffusion time, and further including:

generating an ADC ratio map based on a ratio of the OGSE ADC map to the PGSE ADC map;

generating a MIP image based on the ratio ADC map; and generating an inverted MIP image based on the MIP image of the ratio ADC map, wherein the inverted MIP image includes the seed point map.

14. The computer-implemented method of claim 12, wherein the PGSE has a first diffusion time, the OGSE has a second diffusion time, the first diffusion time is longer than the second diffusion time, and further including:

generating a first trace weighted map based on the first ADC map and a second trace weighted map based on the second ADC map generating a ratio trace weighted map based on the first trace weighted map and the second trace weighted map;

generating a MP image based on the ratio trace weighted map; and generating an MIP image based on the MIP image of the ratio of the trace weighted map, wherein the MIP image includes the seed point map.

15. The computer-implemented method of claim 12, further including:

controlling the gradient coils and the RF transmit coil based on a PGSE DTI sequence with one or more different b-values greater than zero;

processing second MR signals generated in response to the PGSE DTI sequence and received by the RF receive coil to generate one FA map and one ODF map, by using the PGSE DTI data with one or more b-values greater than zero; and generating the tractogram based on the FA map, the ODF map, and a user input indicative of one or more seed points determined from the seed point map.

16. A computer readable storage medium encoded with computer executable instructions, which when executed by a processor, causes the processor to:

control gradient coils and RF transmit coil of an MR imaging system based on a first sequence that includes a PGSE acquisition and an OGSE acquisition;

process first MR signals generated in response to the PGSE and OGSE acquisitions and received by an RF receive coil of the MR imaging system to generate a first ADC map for the PGSE acquisition and a second ADC map for the OGSE acquisition; and generate a seed point map based on the first and second ADC maps, wherein the seed point map visually distinguishes tumor and vasogenic edema.

17. The computer readable storage medium of claim 16, wherein the instructions further cause the processor to generate a tractogram based on the seed points determined from the seed point map, and the tractogram includes a nerve fiber extending from the seed points through the vasogenic edema.

18. The computer readable storage medium of claim 17, wherein the PGSE has a first diffusion time, the OGSE has a second diffusion time, the first diffusion time is longer than the second diffusion time, and the instructions further cause the processor to:

generate a ratio ADC map based on a ratio of the OGSE ADC map to the PGSE ADC map;

generate a maximum intensity projection (MIP) image based on the ratio of the ADC map; and generate an inverted MIP image based on the MIP image of the ratio of the ADC map, wherein the inverted MIP image includes the seed point map.

19. The computer readable storage medium of claim 17, wherein the PGSE has a first diffusion time, the OGSE has a second diffusion time, the first diffusion time is longer than the second diffusion time, and the instructions further cause the processor to:

generate a first trace weighted map based on the first ADC map and a second trace weighted map based on the second ADC map generate a ratio trace weighted map based on the first trace weighted map and the second trace weighted map;

generate a maximum intensity projection (MIP) image based on the ratio trace weighted map, wherein the MIP image includes the seed point map.

20. The computer readable storage medium of claim 17, wherein the instructions further cause the processor to:

control the gradient coils and the RF transmit coil based on a PGSE DTI sequence with one or more different b-values greater than zero;

process second MR signals generated in response to the PGSE DTI sequence and received by the RF receive coil to generate one FA map and one ODF map, by using the PGSE DTI data with one or more b-values greater than zero; and generate the tractogram based on the FA map, the ODF map, and a user input indicative of one or more seed points determined from the seed point map.

* * * * *